United States Patent
Heinberg

(10) Patent No.: US 10,729,465 B2
(45) Date of Patent: Aug. 4, 2020

(54) APPARATUS TO PROTECT THE PELVIC FLOOR DURING VAGINAL CHILDBIRTH

(71) Applicant: PARTURA MEDICAL, INC., Seattle, WA (US)

(72) Inventor: Eric Max Heinberg, Seattle, WA (US)

(73) Assignee: PARTURA MEDICAL, INC., Seattle, WA (US)

( * ) Notice: Subject to any disclaimer, the term of this patent is extended or adjusted under 35 U.S.C. 154(b) by 280 days.

(21) Appl. No.: 15/571,685

(22) PCT Filed: May 11, 2016

(86) PCT No.: PCT/US2016/318580
§ 371 (c)(1),
(2) Date: Nov. 3, 2017

(87) PCT Pub. No.: WO2016/186922
PCT Pub. Date: Nov. 24, 2016

(65) Prior Publication Data
US 2019/0125406 A1    May 2, 2019

Related U.S. Application Data

(60) Provisional application No. 62/162,442, filed on May 15, 2015, provisional application No. 62/208,429, filed on Aug. 21, 2015.

(51) Int. Cl.
*A61B 17/42*    (2006.01)
*A61B 17/44*    (2006.01)
(Continued)

(52) U.S. Cl.
CPC .............. *A61B 17/42* (2013.01); *A61B 5/435* (2013.01); *A61B 17/44* (2013.01); *A61B 90/03* (2016.02); *A61B 2017/00557* (2013.01)

(58) Field of Classification Search
CPC ........... A61B 1/42; A61B 17/44; A61B 5/435; A61B 90/03; A61B 2017/00557
See application file for complete search history.

(56) References Cited

U.S. PATENT DOCUMENTS

| | | |
|---|---|---|
| 5,545,122 A | 8/1996 | Spruill |
| 5,772,630 A | 6/1998 | Ljungquist |

(Continued)

FOREIGN PATENT DOCUMENTS

| | | |
|---|---|---|
| CN | 101115444 A | 1/2008 |
| DE | 42 35 442 A1 | 4/1994 |

(Continued)

OTHER PUBLICATIONS

International Search Report and Written Opinion of the International Searching Authority, dated Aug. 16, 2016, for the International Application No. PCT/US2016/31858, 10 pages.

(Continued)

*Primary Examiner* — Jocelin C Tanner
(74) *Attorney, Agent, or Firm* — Seed Intellectual Property Law Group LLP

(57) ABSTRACT

An apparatus to protect the tissues, muscles and nerves of the female pelvic floor from trauma during vaginal childbirth, the apparatus having a softly expansible intravaginal component capable of insertion into a vaginal canal and under a fetal head while in either a folded or rolled up configuration and to unfold or unroll into a deployed configuration in the vaginal canal and under the fetal head, and a support component with a handle capable of attachment to the intravaginal component, of deploying and inflating the intravaginal, preferably with pressurized air or liquid, and further sized and shaped to provide support and stabilization to at least one from among a perineal, perianal, and anal region when maintained against a female perineal body and perianal region while attached to the intravaginal device that (Continued)

is deployed beneath the fetal head within the vaginal canal, or, in cases of obstructed vaginal childbirth, being subsequently detached, temporarily leaving in situ within the vagina the deployed, inflated intravaginal component for the purpose of preventing or mitigating the subsequent development of abnormal fistulous communications between the vagina and either the urinary bladder or the rectum or both.

10 Claims, 8 Drawing Sheets

(51) Int. Cl.
  *A61B 5/00* (2006.01)
  *A61B 17/00* (2006.01)
  *A61B 90/00* (2016.01)

(56) References Cited

U.S. PATENT DOCUMENTS

| | | | |
|---|---|---|---|
| 6,168,609 B1* | 1/2001 | Kamen | A61F 5/4553 600/573 |
| 2005/0021080 A1* | 1/2005 | Feuer | A61B 1/303 606/207 |
| 2008/0132908 A1 | 6/2008 | Nguyen | |
| 2008/0154284 A1 | 6/2008 | Varma | |
| 2011/0196382 A1 | 8/2011 | Barrier et al. | |

FOREIGN PATENT DOCUMENTS

| | | |
|---|---|---|
| EP | 2 716 243 A1 | 4/2014 |
| RU | 2 139 736 C1 | 10/1999 |
| WO | 2011/072736 A1 | 6/2011 |
| WO | 2012/050634 A1 | 4/2012 |
| WO | 2015/026774 A1 | 2/2015 |

OTHER PUBLICATIONS

Extended European Search Report, dated Jan. 21, 2019, for corresponding International Application No. PCT/US2016/31858, 8 pages.

* cited by examiner

APPARATUS TO PROTECT THE PELVIC FLOOR DURING VAGINAL CHILDBIRTH

CROSS REFERENCE TO RELATED APPLICATIONS

This application claims the benefit under 35 U.S.C. § 119(e) to U.S. Provisional Application No. 62/162,442 filed on May 15, 2015, and U.S. Provisional Application No. 62/208,429 filed Aug. 21, 2015, which applications are incorporated by reference herein in their entireties.

BACKGROUND

Technical Field

The present disclosure is related to a device and method of using the device that is an aid for vaginal childbirth and, more particularly, to an apparatus that protects and preserves the pelvic floor, including the vaginal canal, and supports and stabilizes at least one from among the perineal, perianal, and anal regions and musculature during vaginal child birth.

Description of the Related Art

Female pelvic floor disorders (PFD's) include pelvic organ prolapse, urinary incontinence and fecal incontinence. These disorders affect up to ⅓ or adult women in the United States and entail considerable detriment to their quality of life, as well as substantial direct and indirect societal costs. It is widely accepted that the primary mechanism of pelvic floor dysfunction is traumatic injury that occurs at the time of vaginal childbirth. Such injury is the result of compression, stretching, tearing, or any combination of these, of pelvic floor nerves (pudendal), muscles (levator ani, coccygeous, transversus perineum, internal and external anal sphincters), and connective tissues (endopelvic fascia). These damaging mechanisms are exacerbated by operative vaginal interventions such as the use of forceps or vacuum extractors.

Obstetric fistula is an abnormal communication between the vagina and either the urinary bladder, or the rectum, or both. This condition is the direct consequence of obstructed labor in which the unrelieved pressure of the fetal head against the delicate tissues of the vagina and pelvic floor causes local tissue death that results in large tissue defects and leaves women permanently incontinent of either urine, or feces, or both. The condition is most prevalent in the developing world, especially sub-Saharan Africa and south Asia. According to the World Health Organization (WHO), and estimated 50,000 to 100,000 women develop obstetric fistulas each year and over 2 million presently live with the condition, most of them in their teens or early 20's. Because the condition often results in sociocultural ostacization, obstetric fistula significant entails far reaching physical, social, economic and psychological consequences for those affected.

There currently is no intervention or device of any kind in common use in the field of obstetrics whose purpose is to mitigate or prevent traumatic pelvic floor injury that occurs at the time of vaginal childbirth.

BRIEF SUMMARY

The present disclosure is directed to an apparatus to aid in protecting the female pelvic muscles and nerves during childbirth. In accordance with one aspect of the present disclosure, the apparatus includes an intravaginal device that has a central body having an internal cavity or void, or network of multiple communicating voids, capable of retaining pressurized air or fluid with an input port or multiple ports in fluid communication with the internal void(s), two or more laterally disposed wings extending from the body, each wing having an internal void, or network of multiple voids, capable of retaining fluid, such as a liquid or pressurized air, and in fluid communication with the internal void(s) of the central body, each wing capable of folding or rolling up into a stored configuration when the respective internal void(s), is not pressurized and unfolding or unrolling into a deployed configuration when the respective void(s) is filled with fluid to deploy the device within the vaginal canal and about the presenting fetal head.

In accordance with one aspect of the present disclosure, a first attachment means or mechanism is provided on the body of the intravaginal device, and ideally associated with the input port(s). The handle portion of the device includes a handle sized and shaped to be manually grasped, a fluid delivery device, such as a manual or automated inflation pump having a pump lever or bulb or automated mechanism attached to or contained within the handle and capable of pivotal movement, the manual or automated pump having an output port or multiple ports and structured to provide fluid, such as pressurized air or liquid, to the input port(s) on the body of the intravaginal device in response to either manual actuation of the pump lever or initiation of the automated pump mechanism.

In accordance with another aspect of the present disclosure, a second attachment means or mechanism is provided on the handle or lever or bulb, and ideally associated with the output port(s), and is structured to releasably couple to the first attachment mechanism on the intravaginal device or component of the device and to couple the output port(s) from the manual or automated fluid pump in sealing engagement to the input port(s) of the intravaginal device body.

In accordance with another aspect of the present disclosure, lateral each wing has a distal end that in the deployed configuration extends at an angle away from the intravaginal device's central body and out of a plane of the device's central body to cooperate with the contour of the vaginal canal and form a soft cradle around the presenting fetal head.

In accordance with a further aspect of the present disclosure, the forward handle is structured to provide stabilizing perineal, perianal and anal sphincter support when attached to the intravaginal device.

In accordance with still yet another aspect of the present disclosure, an apparatus is provided that is directed to protecting the female pelvic floor during vaginal delivery. The apparatus includes an intravaginal device capable of insertion into a vaginal canal and under a fetal head while in either a folded or rolled up configuration and to unfold or unroll into a deployed configuration within the vaginal canal and about the fetal head, and a handle device capable of attachment to the intravaginal device, of deploying the intravaginal device, and further sized and shaped to provide support and stabilization to the perineal, perianal and anal regions either when used alone or when attached to the intravaginal device that is deployed within the vaginal canal.

In accordance with still yet another aspect of the present disclosure, the intravaginal device includes a central body having an internal void, or network of multiple communicating voids, capable of retaining fluid, such as pressurized air or liquid, and an input port(s) in fluid communication with the internal void(s), two or more laterally disposed wings extending from the body, each wing having an internal void capable of retaining the fluid and in fluid communication with the internal void or voids of the central body, each wing capable of folding up or rolling up into a stored configuration when the respective internal void(s) is not filled with fluid and unfolding or unrolling into a deployed configuration in which the central body and lateral wings deploy beneath the fetal head when the respective void(s) is filled with fluid, and a first attachment mechanism associated with the body and the input port(s). As such, the device is deployed within or inside the vaginal canal during childbirth to protect the pelvic floor nerves and musculature as well as perineal, perianal, and anal tissues.

In accordance with yet a further aspect of the present disclosure, the handle device ideally includes a fluid delivery device, such as a handle sized and shaped to be manually grasped, a manual or automated pump for air or liquid and having a pump lever or bulb or activation switch attached to or contained within the handle and capable of pivotal movement, the manual or automated pump having an output port(s) and structured to provide fluid to the input port(s) in the body in response to manual actuation of the pump lever or bulb, or automated pump actuation, and a second attachment mechanism associated with the handle and the output port(s) and structured to releasably couple to the first attachment mechanism on the intravaginal device and couple the output port(s) from the pump in sealing engagement to the input port(s) of the intravaginal device body.

Ideally, each of the lateral wings has a distal end that in the deployed configuration extends at an angle away from the intravaginal device's central body and out of a plane of the central body to cooperate with the device body and form a soft cradle around the presenting fetal head, and the handle is structured to provide perineal, perianal, and anal support when attached to the intravaginal device.

In accordance with a method of the present disclosure, an intravaginal device is inserted into a vaginal canal and beneath a fetal head in the vaginal canal during vaginal childbirth, a handle having a manual or automated pump for air or fluid and a perineal/perianal/anal support is attached to the intravaginal device to provide and maintain support and stabilization to the perineal/perianal/anal regions during vaginal childbirth, and the pump is manually or automatically actuated to inflate the intravaginal device with air or liquid and deploy lateral wings on the intravaginal device to stabilize, support and protect the female pelvic floor during vaginal childbirth In accordance with still yet another aspect of the present disclosure, a method of using an apparatus to protect the female pelvic floor during vaginal delivery is provided. The apparatus includes an intravaginal device capable of insertion into a vaginal canal and under a fetal head while in either a folded or rolled up configuration and to unfold or unroll into a deployed configuration in the vaginal canal and beneath the fetal head, and a handle device capable of attachment to the intravaginal device, of deploying the intravaginal device, and further sized and shaped to provide and maintain support and stabilization to the perineal/perianal/anal regions when attached to the intravaginal device that is deployed within the vaginal canal. The method includes the steps of:

inserting the intravaginal device into the vaginal canal and beneath the fetal head within the vaginal canal;

attaching the handle with manual or automated pump and perineal/perianal/anal support to the intravaginal device to provide and maintain support and stabilization to the perineal/perianal/anal regions; and manually or automatically actuating the pump and inflating the intravaginal device with air or liquid to deploy posteriorly and laterally the central body and lateral wings and protect the female pelvic floor musculature and perineal/perianal/anal tissues during vaginal childbirth.

In accordance with a further aspect of the present disclosure, a method of using an apparatus in instances of obstructed vaginal childbirth to temporarily protect the vaginal tissues from ischemic trauma and potentially prevent or mitigate the subsequent development of abnormal fistulous communications between the vagina and either the urinary bladder or rectum or both is provided. The apparatus includes an intravaginal device or component capable of insertion into a vaginal canal and under a fetal head while in either a folded or rolled up configuration and to unfold or unroll into a deployed configuration within the vaginal canal and beneath the fetal head, and a perineal/perianal/anal component with a handle capable of attachment to the intravaginal component, of inflating and deploying the intravaginal device that is sized and shaped to provide support and stabilization to a perineal/perianal/anal region when maintained against a female perineal body and perianal/anal regions while attached to the intravaginal component that is deployed within the vaginal canal. The method includes the following steps:

deploying the intravaginal device into the vaginal canal and under the fetal head in the vaginal canal;

attaching the handle with pump and perineal/perianal/anal support to the intravaginal device;

manually or automatically actuating the pump and inflating the intravaginal device with air or fluid to deploy the device body and lateral wings in order to protect the vaginal tissues from pressure necrosis/ischemic trauma during instances of obstructed vaginal childbirth; and detaching the handle with pump and perineal/perianal/anal support from the deployed, inflated intravaginal component and leaving that deployed, inflated intravaginal component in situ for some limited length of time while transportation from one level of obstetrical care to a higher level of obstetrical care is effected.

As will be readily appreciated from the foregoing, when deployed into the vaginal canal and maintained against the patient's perineum by the operator at the time of vaginal childbirth, the apparatus protects and preserves pelvic floor nerves, muscles and connective tissues, and anal sphincter complex, in several important ways. Firstly, the apparatus will substantially reduce the coefficient of friction between the vaginal mucosal surface and the fetal parts by temporarily increasing vaginal caliber and providing a virtually frictionless (for example, hydrophilic or hydrophobic or colloidal or nanostructured particle coated) surface through which the fetus will pass. Secondly, the design, construction, and materials of the deployed intra-vaginal device will actively deflect and redistribute posterior force vectors of the descending fetus antero-laterally away from the anal sphincters and centrally located vital structures of pelvic floor function and support. Thirdly, the perineal/perianal/anal portion of the device will allow the operator to directly support and stabilize the perineal, perianal, and anal regions in order to protect the muscles and nerves of the anal sphincter complex against any potentially damaging remaining posterior force vectors. Fourthly, for instances of obstructed vaginal childbirth the vaginally inserted, deployed, partially or fully inflated intravaginal component may be detached from the handle with the pump and perineal/perianal/anal support and left in situ within the vaginal canal beneath the fetal head for limited periods of time (4-12 hours) in order to prevent or mitigate ischemic pressure necrosis/ischemic trauma of the vaginal tissues that results in the creation of obstetric fistula from the vagina to either the urinary bladder or rectum or both. The device is ultimately removed at the time of either vaginal or cesarean surgical delivery of the fetus or after 12 hours have elapsed, whichever comes first.

BRIEF DESCRIPTION OF THE SEVERAL VIEWS OF THE DRAWINGS

The foregoing and other features and advantages of the present disclosure will be more readily appreciated as the same become better understood from the following detailed description when taken in conjunction with the accompanying drawings, wherein.

DETAILED DESCRIPTION

Figure 1:
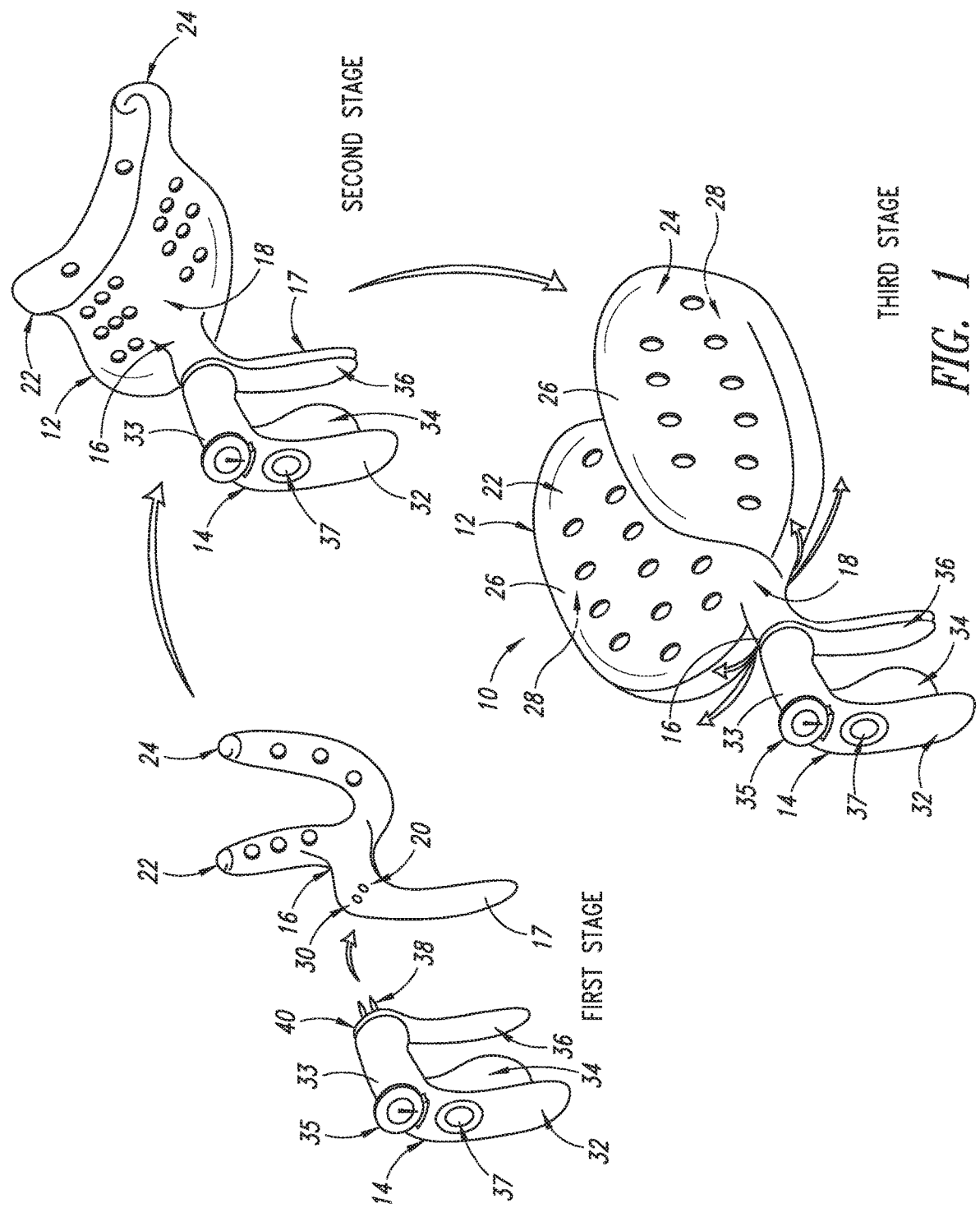
FIG. 1 is an illustration of three stages of configuring and using one implementation of the apparatus of the present disclosure.

In the following description, certain specific details are set forth in order to provide a thorough understanding of various disclosed implementations. However, one skilled in the relevant art will recognize that implementations may be practiced without one or more of these specific details, or with other methods, components, materials, etc. In other instances, well-known structures or components or both associated with manual or automated pumps of air or fluid, ergonomic handles, connection mechanisms, and the structure of internal voids with and without air or fluid channels have not been shown or described in order to avoid unnecessarily obscuring descriptions of the implementations.

Unless the context requires otherwise, throughout the specification and claims that follow, the word "comprise" and variations thereof, such as "comprises" and "comprising" are to be construed in an open inclusive sense, that is, as "including, but not limited to." The foregoing applies equally to the words "including" and "having."

Reference throughout this description to "one implementation" or "an implementation" means that a particular feature, structure, or characteristic described in connection with the implementation is included in at least one implementation. Thus, the appearance of the phrases "in one implementation" or "in an implementation" in various places throughout the specification are not necessarily all referring to the same implementation. Furthermore, the particular features, structures, or characteristics may be combined in any suitable manner in one or more implementations.

By way of introduction, an apparatus and method of using the apparatus is provided to be utilized at the time of vaginal delivery of a fetus so as to prevent and reduce any damage to the tissues, muscles and nerves of the maternal pelvic floor. In accordance with one implementation of the present disclosure, the apparatus consists of 2 devices or components, one intravaginal (IC) and one perineal (PC). For use, these 2 components are sequentially coupled together by the operator in order to first, deploy the IC and second, manually stabilize the patient's perineum/perianal/anal regions by holding and controlling the PC if the operator so chooses.

The IC is an expansible element configured in the form of a "manta ray" and is constructed of ultra thin, flexible, and strong medical grade material such as a specialized medical polymer, polyurethane, polyethylene, polyethylene terephthalate, polytetrafluoroethylene, nylon, silicone, latex, polyvinyl chloride, thermoplastic elastomer, elastic materials, biosynthetic materials, radiopaque materials and combinations thereof. Ideally, the material used for the IC would be both ultra thin and inelastic, so as to maintain its form within the vaginal canal and resist high inflation pressures. In profile, the IC is stiffest at its central portion, where maximal downward forces from the presenting fetal part occur, progressively thinning out laterally to give more flexibility to its "wing tips". Prior to deployment, the IC is in the shape of a cylindrical tube that has a closed distal end and an open proximal end that slides over a projection from a PC handle that contains a pump and output ports. The tube has one or more collapsed wings on each lateral side, that are folded "accordion style" against the central body of the IC and contained there by a thin plastic sleeve (The plastic sleeve ruptures yet remains attached to the proximal/extravaginal portion of the IC as the IC is inflated). The projection on the handle is shaped anatomically with a forwardly descending gentle slope that is slightly spatula-like at the end, similar to the distal end of a weighted gynecologic speculum. The un-inflated tube is slipped over this projection, simultaneously coupled to the output port or ports on the handle, and, after lubricating, both inserted beneath the presenting fetal head. The pump is actuated and air or fluid pumped into the IC causing the lateral wings to inflate and deploy posteriorly and laterally, conforming to the vaginal contours and gently cradling the fetal head so as to protect the vaginal and pelvic tissues. The operator may choose to maintain the handle coupled to the IC so as to actively support and stabilize the perineal/perianal/anal tissues, or remove the handle leaving the inflated IC in situ during the delivery to act as a passive barrier to pelvic floor trauma.

Alternatively, the IC could come in a rolled, front-to-back configuration resembling a small, flexible "cigar" tube. In this form, it is placed just inside the vaginal introitus, coupled to the output port or ports of a PC handle lacking a forward projection, and then inflated, allowing it to deploy forward into the vagina beneath the presenting fetal head.

The IC is of bi-laminar construction with the aspect in contact with vaginal surface being configured so as to resist displacement by the patient's expulsive forces, while the surface in contact with fetal parts is coated with a specialized layer that renders it virtually frictionless. Contained within the space between the two layers of the IC is a lattice of small channels that, when inflated with air or fluid, causes the folded or rolled IC to deploy by unfolding or unrolling forward, upward and laterally (the "manta ray" swimming with wing tips up) into the potential space between the vaginal surface and the fetal presenting part. Depending on which IC deployment configuration is used, the device contains at either its proximal or distal aspect a "female"

mechanism for coupling to the PC and consisting either of a single, or multiple inflation ports that, when coupled with the PC permit ingress of air or fluid for device deployment.

The PC consists of a strong, light ergonomic handle with a smoothly flattened and anatomically curved surface on the side facing the patient. Its design will permit the operator to hold it with either an upward or downward facing grip. Depending on which IC deployment configuration is used, the PC may or may not have a gently sloping forward projection. Contained within the grip is a standard inflation bulb or pump lever for manual inflation, or an automated pump mechanism, along with a pressure gauge that allows the operator to monitor the IC pressure in order to achieve and confirm proper IC deployment while avoiding over-inflation and/or IC rupture. For passive use, valve stopcock will allow for decoupling of the PC from the deployed IC without losing inflation pressure and allowing it to remain in situ. A safety valve within the PC will open automatically if the device is over-inflated in order to prevent IC rupture.

For deployment, the "male" coupling mechanisms of the PC output port or ports are securely mated to the "female" input port(s) of the IC, either prior to insertion as in the primary "accordioned" deployment configuration, or once placed inside the vaginal opening in the case of the secondary "rolled" configuration. The pump is then actuated while maintaining the PC against patient's perineum and perianal region. As it inflates, the IC will sequentially deploy (either by unrolling forward or extending laterally from the central portion) while expanding upward and outward beneath the fetal head within the vaginal canal to form a soft, supportive, air-filled stent within the vaginal canal. Once the coupled device is fully deployed, the operator may elect to use one hand to control the perineum and perianal/anal regions and support the patient's pelvic floor throughout the birthing process, or detach the PC, leaving the inflated IC in situ to provide passive pelvic floor protection. Once the operator determines that the device has served its purpose, it may be allowed to fall out of the vagina as delivery of the fetal body is accomplished.

It will be appreciated that the lateral wings of the IC are not the only thing that protect the pelvic floor. The central portion of the IC is sized and shaped to deflect forces laterally and anteriorly toward the wings where there are few vital structures that those forces can damage Referring next to FIG. 1, shown therein are isometric views of the stages of deployment of an apparatus 10 formed in accordance with the present disclosure in a fully deployed configuration that is directed to protecting the pelvic floor during vaginal delivery. The apparatus 10 includes an intravaginal device or component 12 capable of insertion into a vaginal canal and under a fetal head while in either a folded or rolled up configuration and to unfold or unroll into a deployed configuration within the vaginal canal and under the fetal head. The apparatus 10 further includes a handle device 14 with a support component 36 capable of providing support to at least one from among the perineal, perianal, and anal regions and musculature, the handle device 14 capable of attachment to the intravaginal component 12. The handle device is structured to deploy the intravaginal component 12 as shown in the three stages in FIG. 1. It is further designed to use the support component 36 to provide support and stabilization to the at least one from among the perineal, perianal, and anal regions when left attached to the intravaginal device 12 after it is deployed within the vaginal canal.

The intravaginal component 12 includes a central body 16 having a first perineal/perianal/anal support component 17 ("first support component 17") extending therefrom and an internal cavity or void 18 capable of retaining pressurized air or fluid and input ports 20 in fluid communication with the internal void 18 and providing support to one or more of the perineal, perianal, and anal regions and musculature. Laterally disposed wings 22, 24 extend from the central body 16, each wing 22, 24 having a distal end 26 and contiguous internal voids 28 capable of retaining pressurized air or fluid and in fluid communication with the internal void 18 of the body 16. Each wing 22, 24 is capable of folding or rolling up into a stored configuration (shown in FIG. 2) when the respective internal void 28 is not pressurized with air or fluid and unfolding or unrolling into a deployed configuration (shown in FIG. 1) when the respective void 18 is filled with pressurized air or fluid. The intravaginal component 12 also includes a first attachment mechanism 30 associated with the body 16, in this case the input port 20 as described more fully below.

The handle device 14 ideally includes a handle or hand grip 32 extending from a lateral body 33 and sized and shaped to be manually grasped. A manual or automated pump for air or liquid or other fluid 34 is attached to and extends from the handle device 14. Ideally, the handle is capable of pivotal movement. The pump 34 has output ports 38 structured to provide pressurized air or other fluid to the input ports 20 on the device body 16 in response to actuation of the pump 34.

A second perineal/perianal/anal support component 36 ("second support component 36") extends from the main handle 32, preferably downward and parallel to the first support perineal/perianal/anal component 17 and hand grip 32 and is structured to provide stabilizing support for at least one from among the perineal, perianal, and anal areas when attached to the intravaginal component 12 and in use. Preferably the first support component 17 nests with the second support component 36 when the apparatus 10 is in use as shown in the third stage of FIG. 1.

A second attachment mechanism 40 is associated with the handle 32 and the output port 38 and is structured to releasably couple to the first attachment mechanism 30 on the intravaginal component 12 and couple the output ports 38 from the manual pump 34 in sealing engagement to the input port 20 of the body 16. For example, the second attachment mechanism 40 can be the one or more pegs that function as the output ports 38 extending from the handle device 14, and the first attachment mechanism can be the input ports 20 sized and shaped to receive the output port pegs 38 in slidable engagement, ideally with a snug fit. Thus, the output port pegs 38 also function as nozzles configured to enable the passage of pressurized air or fluid from the pump 34 into the body cavity 18 and wings 22, 24 of the device.

A button 37 is formed in the main handle 32 of the handle device 14 below a pressure gauge 35 that is located on the handle device 14 at the intersection of the hand grip 32 and the body 33. The button 37 is operatively coupled to a proportional valve (not shown) inside the body 33 to enable an operator to control the release of pressurized air or fluid from the intravaginal component 12. The valve is spring loaded into a normally closed position, provides for variable amounts of fluid flow, and is activated when the button 37 is held down part way by the operator, possibly by the operator's thumb. The operator can thereby release as much or as little pressure a necessary. The pressure gauge 35 is in fluid communication with the cavity 18 of the device body and wings 22, 24 and provides a visual indication of the amount of fluid pressure, such as air pressure, in the device body cavity 18 and the wings 22, 24.

In a preferred embodiment, the button 37 facilitates mechanical uncoupling of the handle device 14 from the intravaginal component 12. A latching mechanism associated with the button 37 automatically and releasably latches the intravaginal component 12 to the handle device 14 upon engagement of the intravaginal component 12 to the handle device 14. When the operator pushes the button 37 down all the way until it clicks hard, the latching mechanism unlatches, releasing the handle device 14 from the intravaginal component 12 completely while at the same time maintaining the amount of inflation within the device at that time.

Ideally, the distal end 26 on each lateral wing 22, 24 in the deployed configuration extends at an angle away from the central body 16 of the intravaginal component 12 and out of a plane of that central body 16 to cooperate with the central body 16 and form a compressible, softly structured anatomic cradle or basket-like form within the vaginal canal. The handle 32 is structured with a smoothly contoured surface anterior to the operators gripping fingers that can be maintained with gentle pressure against the female perineal body, perianal tissues and anus in order to provide perineal, perianal and anal stabilization and support while it remains attached to the deployed, inflated intravaginal device 12.

Figure 2:
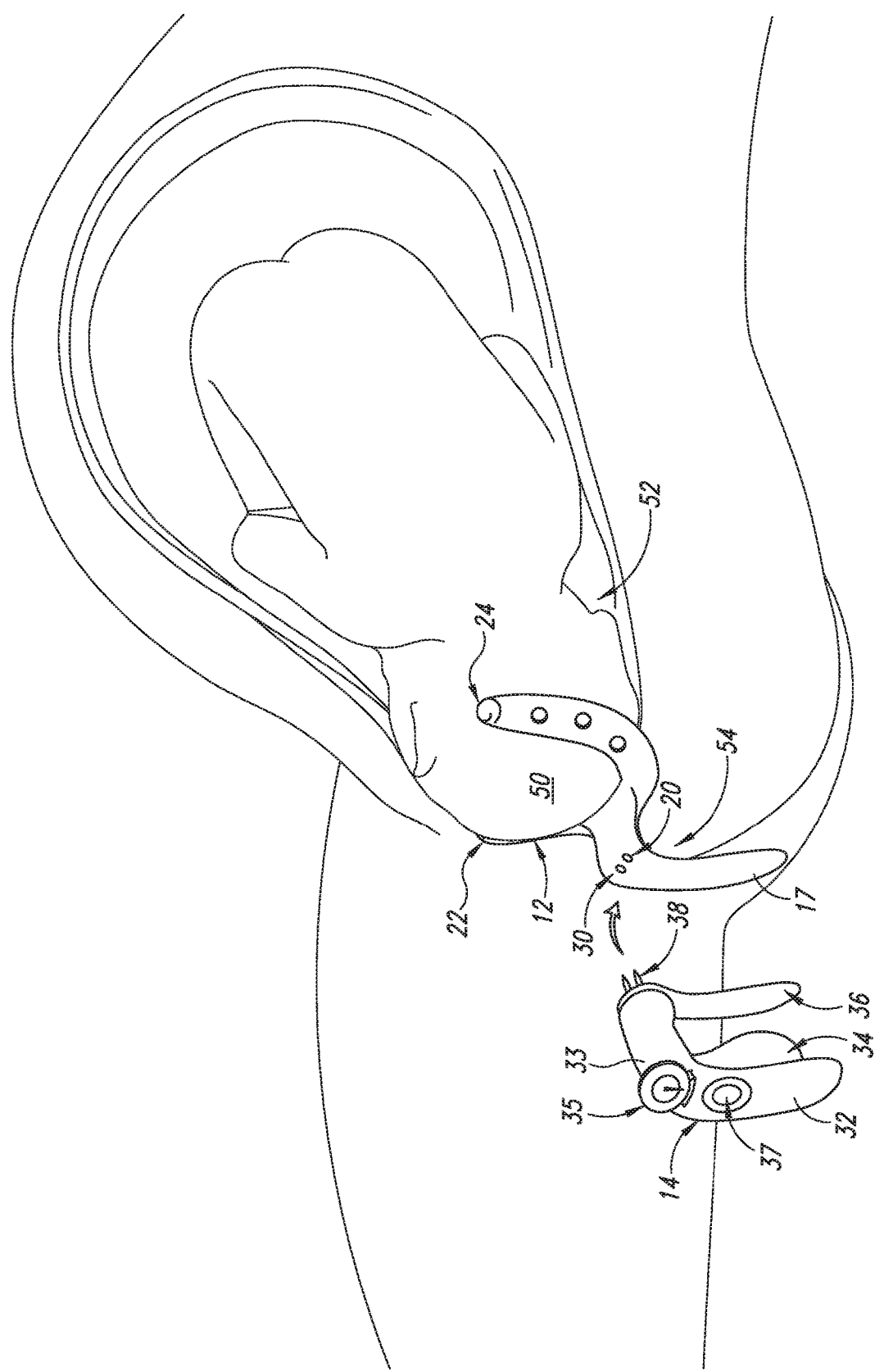
FIG. 2 illustrates a first step of placement of the intravaginal device in the vaginal canal and beneath a fetal head.

FIG. 2 shows the apparatus 10 in use with a fetal head 50 within the vaginal canal 52. The perineal/perianal area 54 is supported by the first support component 17 when the uninflated intravaginal device 12 is deployed into position below the crown of the fetal head 50 at the vaginal canal 52. The handle device 14 is attached to the intravaginal device 12 by inserting the pegs 38 into the ports 20 whereby the first and second support components 17, 36 are in an abutting and preferably nested position.

Figure 3:
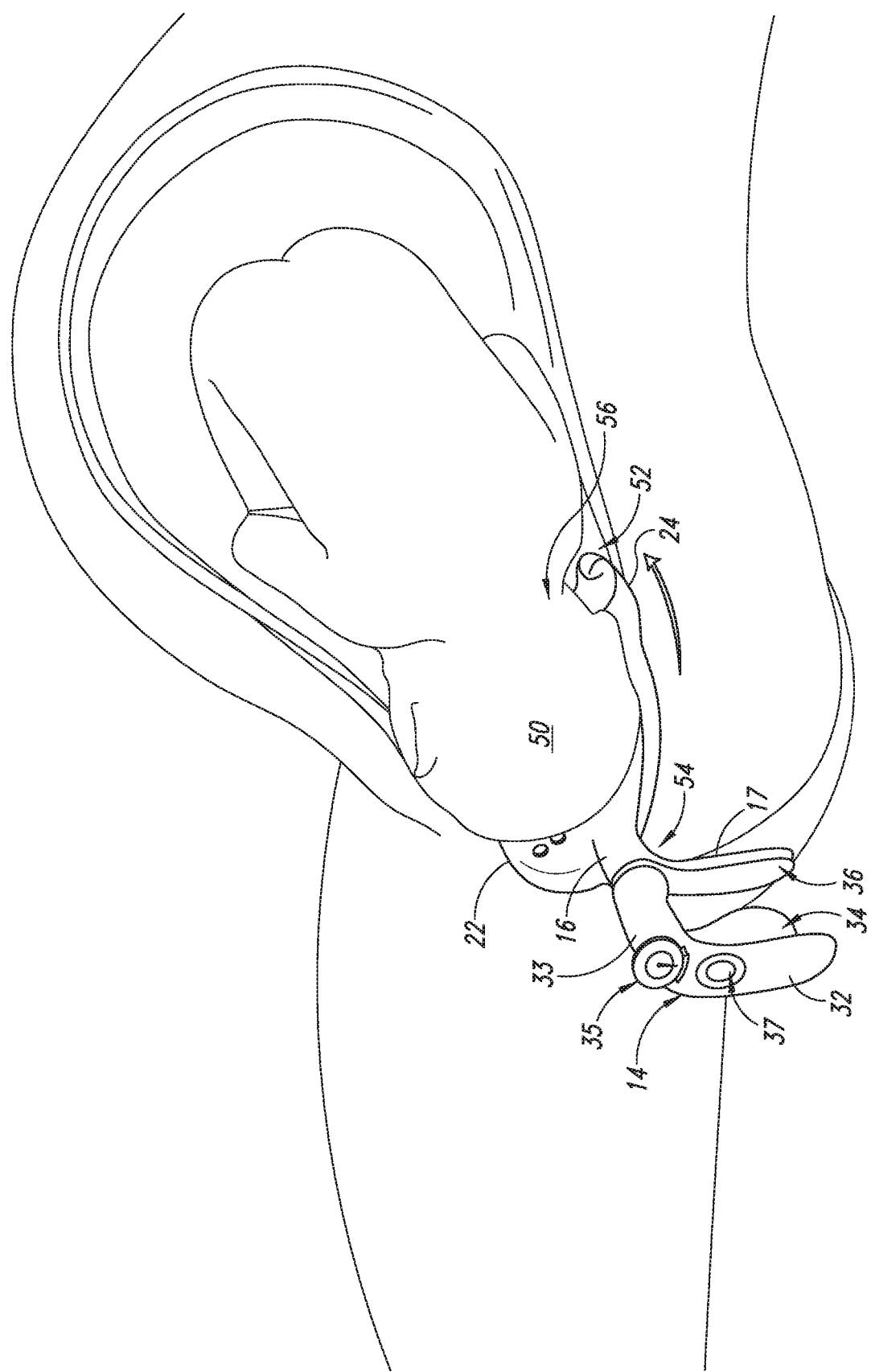
FIG. 3 illustrates a second step of attaching the handle and deploying the intravaginal device in the vaginal canal and beneath the fetal head.

The pump 34 is then actuated to cause the intravaginal device 12 to inflate as shown in FIG. 3. As they inflate, the device body 16 and lateral wings 22, 24 will be filled with air or fluid, causing the body 16 to unroll along with the wings 22, 24 and deploy into the vaginal canal 52 and beneath the fetal head 50. The length of the device body 16 is such that it will terminate at or above the fetal neck 56 area when fully inflated.

Figure 4:
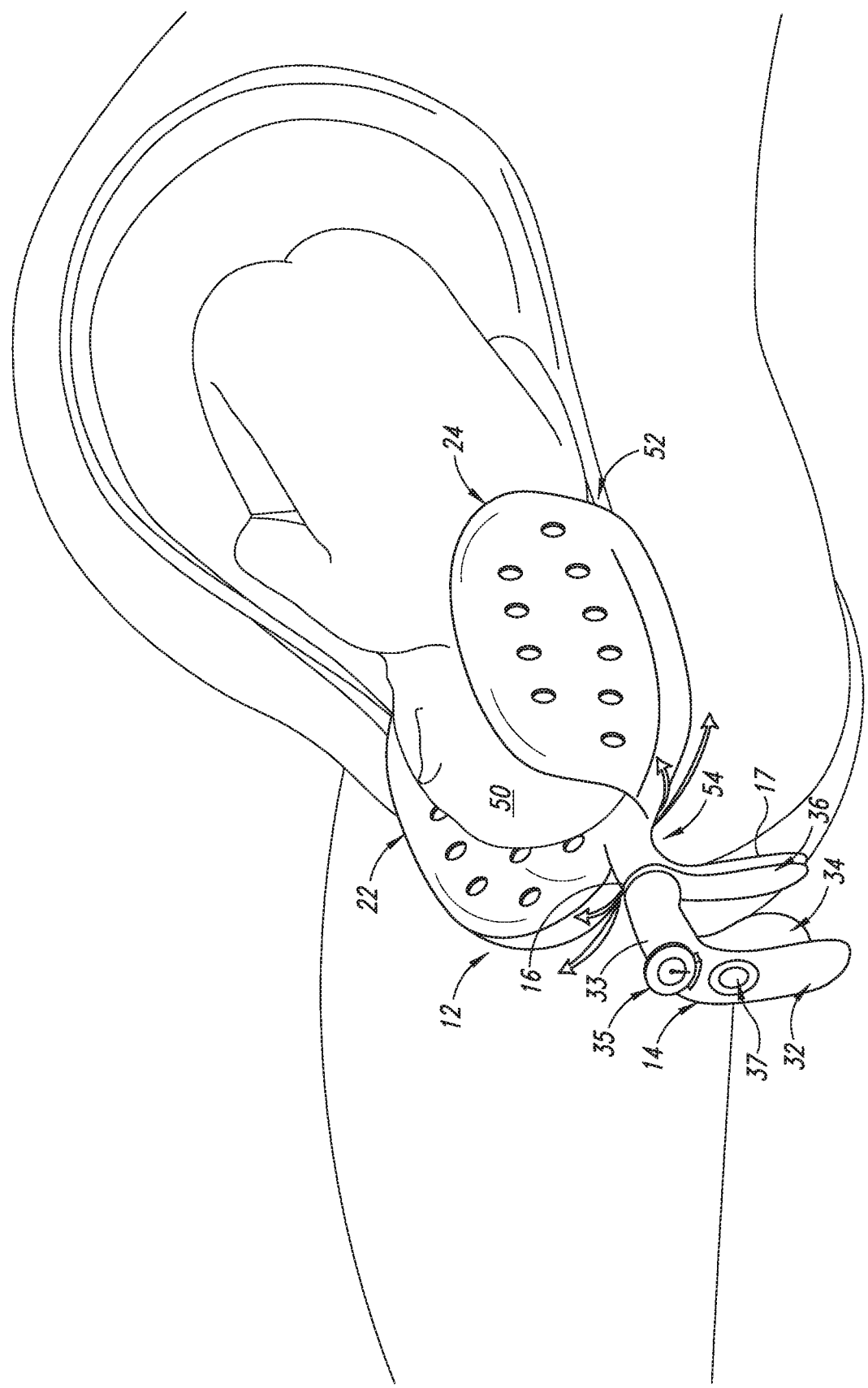
FIG. 4 illustrates the fully deployed apparatus in a vaginal canal and under the fetal head.

FIG. 4 illustrates the apparatus 10 in the fully inflated and deployed configuration. The device body 16 is completely unrolled and inflated as are the lateral wings 22, 24. The first and second support components 17, 36 provide support to at least one from among the perineal, perianal, and anal regions and musculature 54 and to the floor and walls of the vaginal canal 52.

Figure 5:
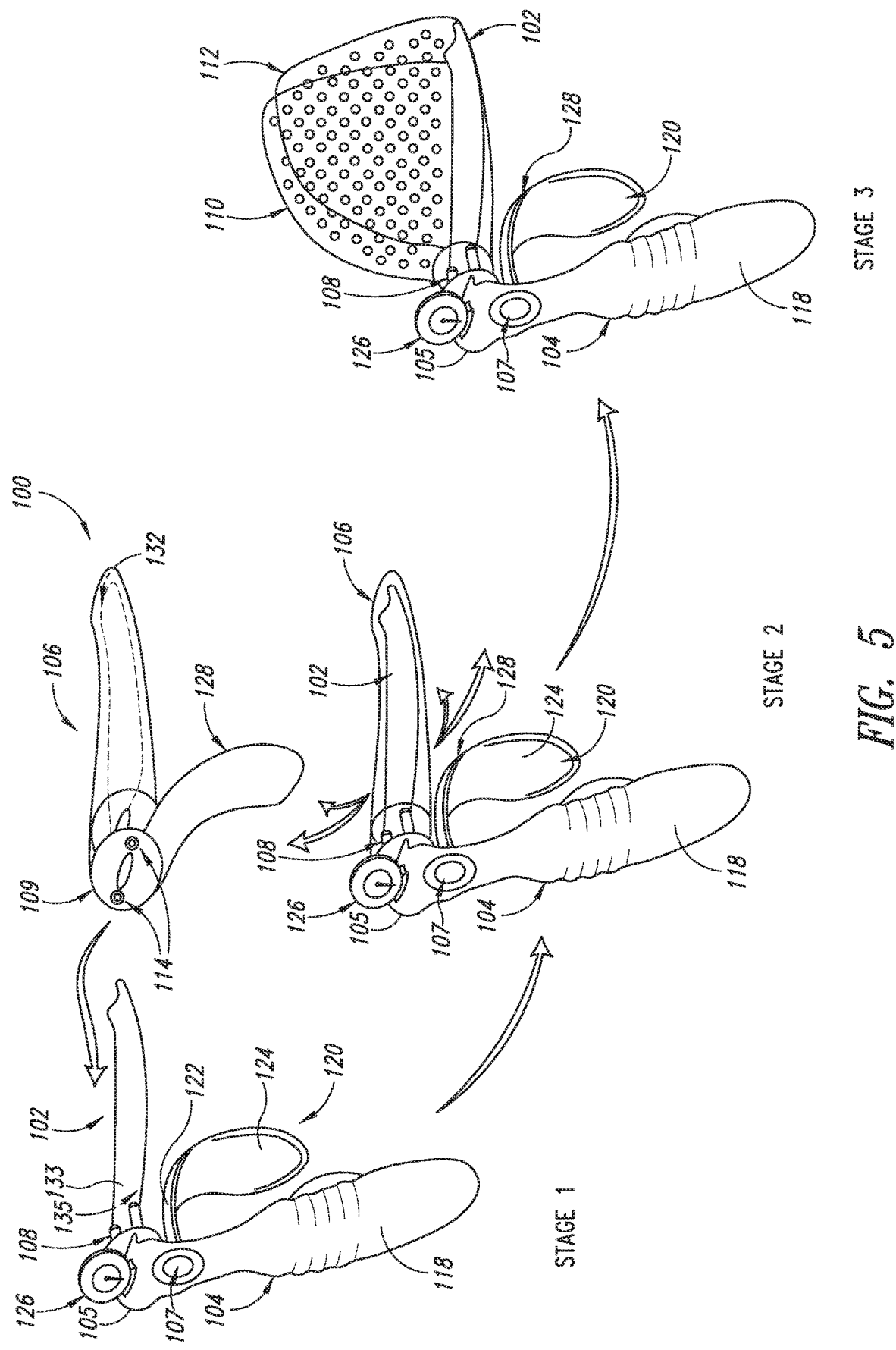
FIG. 5 is an illustration of three stages of configuring and using a preferred implementation of an apparatus of the present disclosure that includes a planar insert or projection.

In an alternative, preferred implementation the wings can be configured to expand laterally outward from the device body in an accordion-like fashion as shown in FIG. 5. FIG. 5 is an illustration of three stages of configuring and using a preferred implementation of an apparatus 100 of the present disclosure that includes an elongated, substantially flat insert or planar projection 102 extending from handle 104. The planar projection 102 is insertable into an inflatable intravaginal component 106 that has an accordion-like configuration contained within an outer plastic sleeve. At the base of the planar projection 102 are one or more coupling output ports as described in the previous embodiment. While there are no output ports along the length of the planar projection, it would be possible to form a fluid passageway in the planar projection without output ports along the length of the planar projection.

The intravaginal device or component 106 has a structured collar 109 coupled to first and second lateral cushioning wings 110, 112 that unfold in an accordion-like manner. Each wing 110, 112 has one or more internal bladders or voids interconnected to each other and inflation ports 114 to receive pressurized air or fluid. As with the previous embodiment, the handle 104 includes an inflation pump 116 that provides pressurized air or fluid through the inflation ports 114 and into the lateral wings 110, 112, when manually or automatically actuated. The wings are preferably in a folded accordion-like configuration when uninflated. Upon inflation, they will deploy laterally and posteriorly within the vaginal canal beneath and around the fetal head to provide protection for the pelvic floor as discussed more fully below in connection with FIGS. 6 and 7.

As shown in Stage 1 of FIG. 5, the handle 104 has a hand grip portion 118 with the inflation bulb 116 extending therefrom and in fluid communication with output ports 108 that extend from a top 105 of the handle 104 at approximately a 90 degree or greater angle. A perineal/perianal/anal support 120 extends from the hand grip portion 118 below the planar projection 102 and in the same direction as the planar projection 102. The support 120 has a lateral arm 122 and a distal leg 124 that extends away from the planar projection 102.

Also formed in the handle 104 is a button 107 having the same function as the button 37 described above. Extending from the top 105 of the handle 104 is a pressure gauge 126 having the same function as the pressure gauge 35 described above. The button 107 facilitates mechanical uncoupling of the handle 104 from the intravaginal component 106. A latching mechanism associated with the button 107 automatically and releasably latches the intravaginal component 106 to the handle device 104 upon engagement of the intravaginal component 106 to the handle device 104. When the operator pushes the button 107 down all the way, i.e., the full extent of its travel, it will cause the latching mechanism to unlatch, releasing the handle device 104 from the deployed intravaginal component 106 completely while maintaining the amount of inflation within the intravaginal component 106 at that time. This can be accomplished by a check valve (not shown) within the inflation ports 114 on the intravaginal device 106.

The intravaginal device 106 shown in stage 1 of FIG. 5 includes a perineal brace 128 extending from the inflation port 114. It is preferably sized and shaped to match the size and shape of the support 120 extending from the handle 104 to allow them to nest together when coupled for IC deployment.

Extending from the structured collar 109 is a unitary structure having a body 130 and the collapsed uninflated lateral wings 110, 112. Internal to the device body 130 is a longitudinal channel 132 sized and shaped to receive the planar projection 102 in slidable engagement. In addition, as shown in FIG. 5, the planar projection 102 has opposing planar sides 133, 135 configured for insertion into the intravaginal component 106 and positioning beneath the fetal head 50 within the vaginal canal 52.

In use, the planar projection 102 is inserted into the channel 132 of the intravaginal component body 130 allowing for secure coupling of the output ports 108 and input or inflation ports 114 at the base of the collar 109. The handle 104 releasably latches to the intravaginal component 106 automatically as described above, which is shown in stage 2 of FIG. 5. In stage 3 of FIG. 5, the inflation bulb 116 is manipulated or actuated to cause pressurized fluid to enter the lateral wings 110, 112, resulting in their inflation to a desired degree of pressure and posterior and lateral deployment within the vaginal canal. The check valve in the fluid passage at the inflation port 114 retains the fluid at the desired pressure level and the lateral wings 110, 112 at the desired amount of inflation. If the operator desires to reduce the amount of inflation, the operator may press the button 107 part way, which maintains the latched engagement but allows fluid to pass out of the intravaginal component 106 and lateral wings 110, 112 to the atmosphere.

Figure 6:
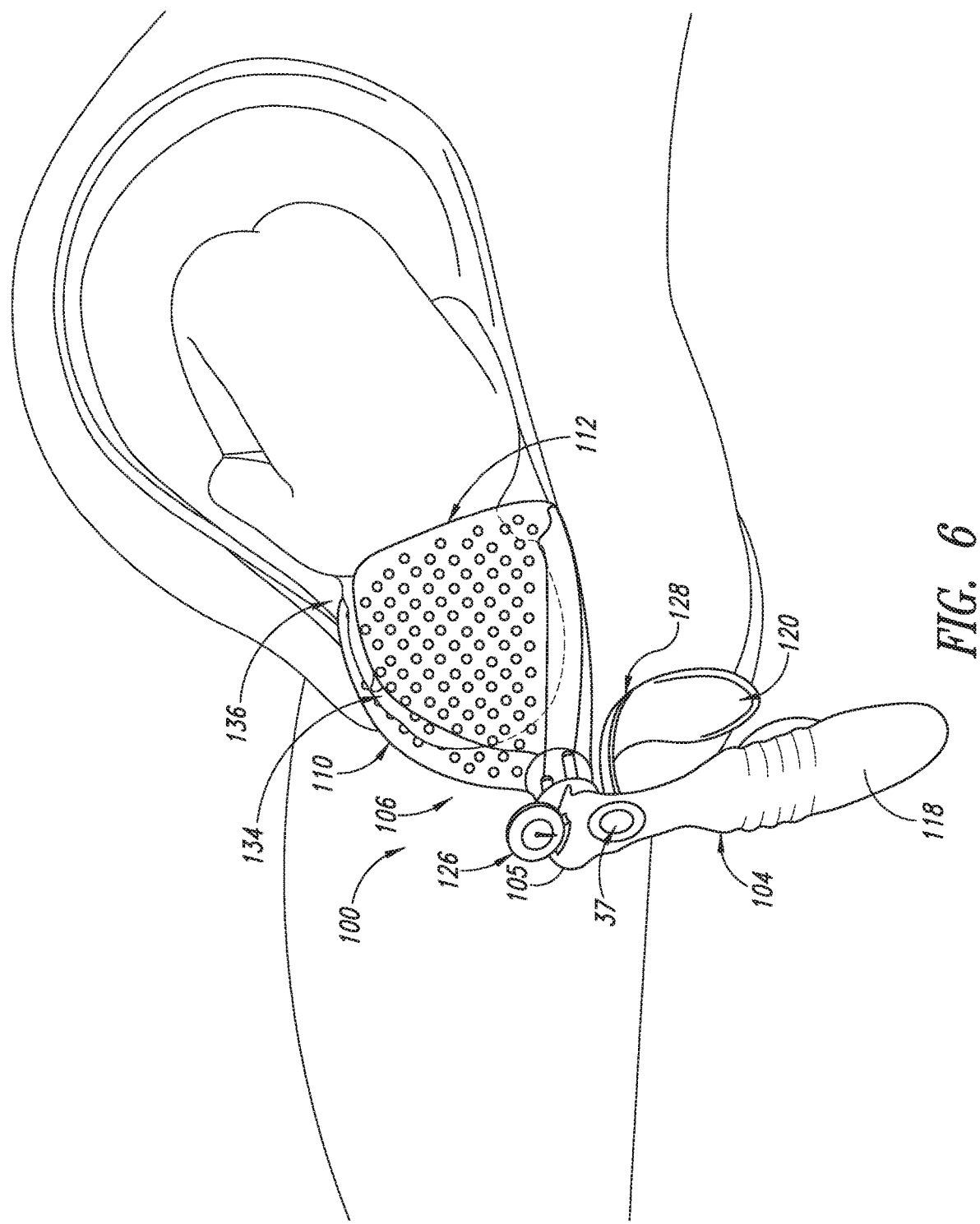
FIG. 6 is an illustration of the apparatus of claim 5 fully deployed in the vaginal canal.

FIG. 6 shows the apparatus 100 with the lateral wings 110, 112 inflated and positioned at least partially around the fetal head 134 in the vaginal canal 136. The handle 104 is shown attached to the intravaginal component 106 and the perineal/perianal/anal support 120 along with the perineal/perianal/anal brace 128 to provide support for at least one from among the perineal, perianal and anal regions, including the musculature and tissues (collectively referred to with reference number 138).

Figure 7:
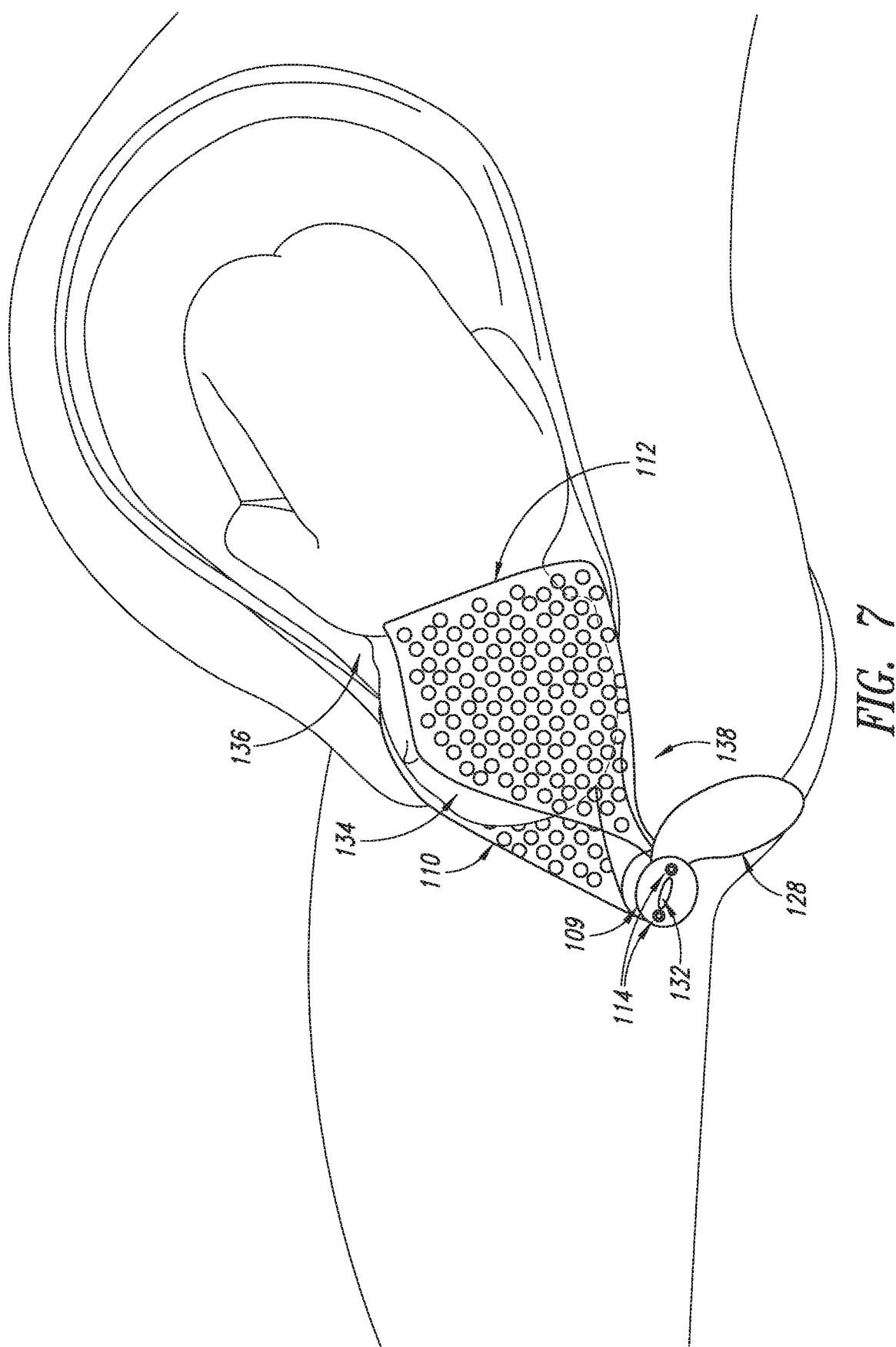
FIG. 7 illustrates the fully deployed intravaginal device with the handle uncoupled therefrom.

Fully pressing the button 107 causes the handle 104 to unlatch from the intravaginal component 106, as shown in FIG. 7, where the handle 104 is removed from the intravaginal component 106 and the internal check valve retains the intravaginal component 106 and lateral wings 110, 112 in their inflated state.

It is to be understood that the device may be used by the operator as a temporizing measure to possibly prevent obstetric fistula during patient transport in cases of obstructed labor when timely cesarean delivery is not possible. This is especially useful in third-world countries where timely access to medical services, supplies, and instruments is not possible or is extremely difficult to obtain.

The various implementations described above can be combined to provide further implementations. Aspects of the implementations can be modified, if necessary to employ concepts of the various patents, applications and publications to provide yet further implementations.

Figure 8:
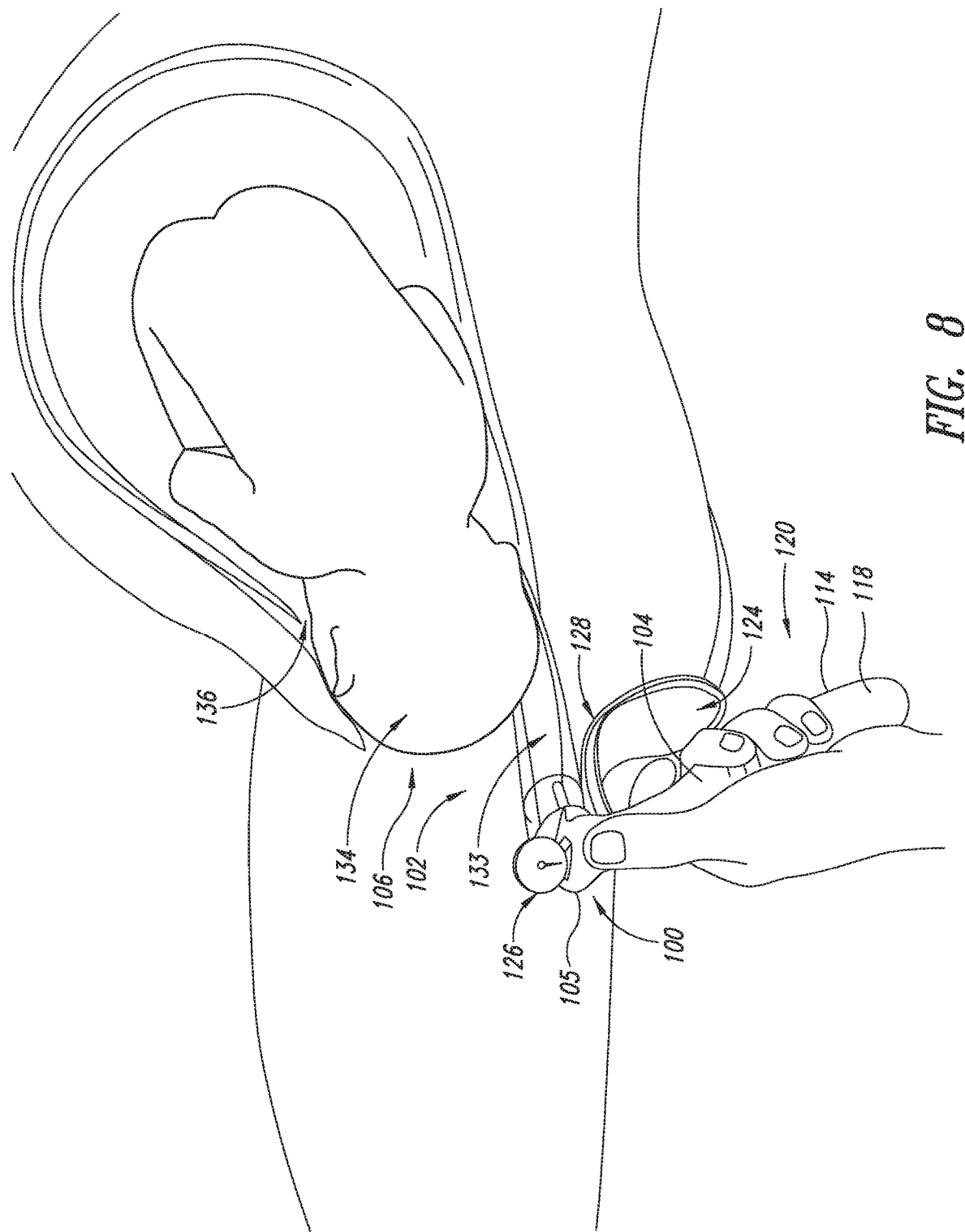
FIG. 8 is an illustration of the apparatus in the vaginal canal under the fetal head without the intravaginal portion.

For example, in cases where deployment of the intravaginal component 106 is not desired, not technically feasible, or in which the intravaginal component 106 is unavailable, the handle device 104 with the forward projection 102 and perineal/perianal/anal stabilizing surface or support 120 may be used alone. The forward projection 102 is inserted into the vaginal canal at the time of delivery and employed by the operator to manually stabilize and protect from birth trauma the vagina, pelvic nerves, perineal body, and anal sphincter musculature. FIG. 8 illustrates the use of the handle 104 with the forward planar projection 102 alone (i.e. without the intravaginal component 106) to mitigate pelvic floor trauma during vaginal delivery. In certain clinical circumstances (narrow vaginal caliber, suspected asynclitic or uncertain position of the fetal head, operator preference) the operator may choose to use the handle 104 of the apparatus 100 by itself such that it need not always be coupled with the intravaginal component 106.

These and other changes can be made to the implementations in light of the above-detailed description. In general, in the following claims, the terms used should not be construed to limit the claims to the specific implementations disclosed in the specification and the claims, but should be construed to include all possible implementations along with the full scope of equivalents to which such claims are entitled. Accordingly, the claims are not limited by the disclosure.

The invention claimed is:

1. An obstetrical apparatus, comprising:
an intravaginal device for obstetrical care that includes:
a central body formed of flexible material and having an expansible intravaginal component with at least one internal void capable of retaining fluid and at least one input port in fluid communication with the at least one internal void;
two or more laterally disposed wings formed of flexible material and extending from the central body, each wing having an internal void capable of retaining fluid and in fluid communication with the at least one internal void of the central body, each wing capable of folding or rolling up into a stored configuration when the respective internal void is not filled with fluid, and unfolding or unrolling into a deployed configuration when the respective void is inflated with fluid;
a first attachment mechanism associated with the central body and the at least one input port; and
a handle device that includes:
a handle sized and shaped to be manually grasped;
a fluid delivery device having at least one output port and structured to provide fluid to the at least one input port on the central body; and
a second attachment mechanism associated with the handle and the at least one output port and structured to releasably couple to the first attachment mechanism on the intravaginal component and couple the at least one output port of the fluid delivery device in sealing engagement to the at least one input port of the central body of the intravaginal component.

2. The apparatus of claim 1 wherein each lateral wing has a distal end that in the deployed configuration extends at an angle away from the central body and out of a plane of the central body to form a compressible structured anatomic cradle.

3. The apparatus of claim 1 wherein the intravaginal device includes a first support component extending therefrom and capable of providing stabilizing support to one or more of the perineal, perianal, and anal regions and musculature; and wherein the handle device includes a second support component that extends from the handle and is sized and shaped to cooperate with the first support component to provide stabilizing support to one or more of the perineal, perianal, and anal regions and musculature.

4. The apparatus of claim 3 wherein the first support component is sized and shaped to nest within the second support component.

5. An obstetrical apparatus to protect a female pelvic floor in a vaginal canal during vaginal childbirth, the apparatus comprising:
an intravaginal device formed of flexible material and capable of being in a folded configuration or rolled up configuration and inserted into the vaginal canal and under a fetal head while the intravaginal device is in either the folded configuration or rolled up configuration and to unfold or unroll into a deployed configuration within the vaginal canal and beneath the fetal head, the intravaginal device including:
a body having at least one internal void capable of retaining fluid, the body further having at least one input port in fluid communication with the at least one internal void;
two or more laterally disposed wings extending from the body, each wing having an internal void capable of retaining fluid and in fluid communication with the at least one internal void of the body, each wing capable of folding or rolling up into a stored configuration when the respective at least one internal void is not filled with fluid and unfolding or unrolling into a deployed configuration when the respective at least one internal void is filled with fluid; and a first attachment mechanism associated with the body and the at least one input port; and a handle device having a second attachment mechanism capable of attachment to the first attachment mechanism on the intravaginal device, the handle device including a fluid delivery device having at least one output port configured to attach to the input port on the intravaginal device and to deliver fluid to the at least one internal void to inflate and deploy the intravaginal device with a fluid, the handle device further including a first support component extending from the handle that is sized and shaped to provide support and stabilization to at least one from among perineal, perianal, and anal regions when attached to the intravaginal device that is deployed and inflated within the vaginal canal to protect the pelvic floor during vaginal childbirth.

6. The apparatus of claim 5 wherein the handle device comprises:

a handle sized and shaped to be manually grasped;

an anatomically contoured forward projection configured to slidably receive the intravaginal device and configured to be slipped beneath the fetal head prior to inflation and deployment; and the second attachment mechanism associated with the handle and the at least one output port and structured to releasably couple to the first attachment mechanism on the intravaginal device and couple the at least one output port on the fluid delivery device in sealing engagement to the at least one input port of the body.

7. The apparatus of claim 6 wherein the fluid delivery device comprises a manual or automated pump having a pump bulb or lever attached to the handle and capable of pivotal movement, the pump coupled to the at least one output port and structured to provide pressurized air or fluid to the at least one input port on the body in response to actuation of the pump lever or bulb.

8. The apparatus of claim 7 wherein each lateral wing has a distal end that in the deployed configuration extends at an angle away from the intravaginal device body and out of a plane of the body to cooperate with the body and form a compressible anatomic cradle within the vaginal canal.

9. The apparatus of claim 5 wherein the intravaginal device includes a second support component extending therefrom and capable of providing stabilizing support to one or more of the perineal, perianal, and anal regions and musculature; and the second support component that extends from the handle is sized and shaped to cooperate with the first support component to provide stabilizing support to one or more of the perineal, perianal, and anal regions and musculature.

10. The apparatus of claim 9 wherein the second support component is sized and shaped to nest within the first support component.

* * * * *